(12) United States Patent
Barciszewski et al.

(10) Patent No.: US 8,946,400 B2
(45) Date of Patent: Feb. 3, 2015

(54) SEQUENCE OF DSRNA: ATN-RNA SPECIFIC FOR TENASCIN-C

(75) Inventors: Jan Barciszewski, Poznan (PL); Miroslawa Barciszewska, Poznan (PL); Leszek Rychlewski, Poznan (PL); Eliza Wyszko, Poznan (PL); Iwona Gawronska, Poznan (PL); Ryszard Zukiel, Poznan (PL); Katarzyna Rolle, Gadki (PL); Stanisaw Nowak, Poznan (PL)

(73) Assignees: Instytut Chemii Bioorganicznej Pan, Poznan (PL); Uniwersytet Medyczny Im.Karola Marcinkowskiego, Poznan (PL); Bioinfobank Sp.Z O.O., Poznan (PL)

( * ) Notice: Subject to any disclaimer, the term of this patent is extended or adjusted under 35 U.S.C. 154(b) by 1323 days.

(21) Appl. No.: 12/375,916

(22) PCT Filed: Jul. 30, 2007

(86) PCT No.: PCT/PL2007/000054
§ 371 (c)(1),
(2), (4) Date: Nov. 17, 2009

(87) PCT Pub. No.: WO2008/016317
PCT Pub. Date: Feb. 7, 2008

(65) Prior Publication Data
US 2010/0076053 A1  Mar. 25, 2010

(30) Foreign Application Priority Data
Jul. 31, 2006 (PL) .......................... 380335

(51) Int. Cl.
*C07H 21/04* (2006.01)
*C12N 15/113* (2010.01)

(52) U.S. Cl.
CPC .......... *C12N 15/1136* (2013.01); *C12N 15/113* (2013.01); *C12N 2310/14* (2013.01)
USPC ...................................................... 536/24.5

(58) Field of Classification Search
USPC ...................................................... 536/24.5
See application file for complete search history.

(56) References Cited

U.S. PATENT DOCUMENTS 6,506,559 B1 * 1/2003 Fire et al. ..................... 435/6.16
6,573,099 B2 * 6/2003 Graham ......................... 435/455

FOREIGN PATENT DOCUMENTS

WO      0006775 A1    2/2000
WO   2005095622 A2   10/2005

OTHER PUBLICATIONS

GenBank Accesion No. NM 0021601 (May 14, 2006), retrieved from www.ncbi.nlm.nih.gov.*

Seki, et al., "Identification of tenascin-C as a key molecule determining stromal cell-dependent erythropoiesis" Experimental Hematology, Apr. 1, 2006, pp. 519-527, vol. 34, Nr. 4.
Reardon, et al., "Phase II trial of murine (131)l-labeled antitenascin monoclonal antibody 81C6 administered into surgically created resection cavities of patients with newly diagnosed malignant gliomas", Journal of Clinical Oncology, Mar. 1, 2002, pp. 1389-1397, vol. 20, Nr. 5, American Society of Clinical Oncology.
Grzelinski, et al., "RNA interference-mediated gene silencing of pleiotrophin through polyethylenimine-complexed small interfering RNAs in vivo exerts antitumoral effects in glioblastoma xenografts", Human Gene Therapy, Jul. 15, 2006, pp. 751-766, vol. 17, Nr. 7.
Jain, "Future prospects for the cure of brain cancer", Technology in Cancer Research and Treatment, Jun. 1, 2006, pp. 183-184, vol. 5, Nr:3, Adenine Press, Schenectady, NY.
Leins, et al., "Expression of tenascin-C in various human brain tumors and its relevance for survival in patients with astrocytoma", Cancer, Dec. 1, 2003, pp. 2430-2439, vol. 98, Nr. 11, American Cancer Society, Philadelphia, PA.
Behrem, et al., "Distribution pattern of tenascin-C in glioblastoma: Correlation with angiogenesis and tumor cell proliferation", Pathology Oncology Research, Jan. 1, 2005, pp. 229-235, vol. 11, Nr. 4,Tud. Kiado, Budapest, HU.
Zukiel, et al., "Supression of human brain tumor with interference RNA specific for tenascin-C", Cancer Biology and Therapy, Aug. 1, 2006, pp. 1002-1007, vol. 5, Nr. 8, Landes Bioscience.
Van Den Bent, M.J. et al., "Current and Future Trials of the EORTC Brain Tumor Group", Onkologie 2004; 27:246-50.
Chiquet-Ehrismann, Ruth, et al., "Tenascins: Regulation and Putative Functions During Pathological Stress", Journal of Pathology 2003; 200: 488-489.
Hicke, Brian J., et al., "Tenascin-C Aptamers are Generated Using Tumor Cells and Purified Protein", Journal of Biological Chemistry 2001; 276:48644-54.
Pas, J., et al., "Analysis of Structure and Function of Tenascin-C", Int. J. of Biochem. Cell Biol. 2006, 38(9): 1594-602.
Prawitt, D., et al. "RNAi Knock-Down Mice: An Emerging Technology for Post-Genomic Functional Genetics", Cytogenetic Genome Research 2004; 105:412-421.
Caplen, NJ, "Gene Therapy Progress and Prospects. Downregulating Gene Expression: The Impact of RNA Interference", Gene Therapy 2004; 11:1241-8.
Hall, J., "Unravelling the General Properties of siRNAs: Strength in Numbers and Lessons from the Past", Nature Reviews Genetics 2004; 11:1241-8.

(Continued)

*Primary Examiner* — Jon E Angell
(74) *Attorney, Agent, or Firm* — Christopher L. Parmelee; Walker & Jocke

(57) ABSTRACT

The subject matters of this invention are a sequence of double-stranded RNA: ATN-RNA, intervention using interference RNA (iRNAi), use of a sequence of double-stranded RNA: ATN-RNA, a method of treating a brain tumor and a method of inhibiting a brain tumor cells which express tenascin, a kit for inhibiting cancer cell which expresses tenascin and a method for a kit preparation in a brain tumor therapy. Malignant gliomas preferentially express a number of surface markers that may be exploited as therapeutic targets, including tenascin-C, an extracellular matrix glycoprotein that is ubiquitously expressed by malignant gliomas and probably contributes to tumor cell adhesion, invasion, migration and proliferation. For tenascin-C inhibition, RNA interference intervention (iRNAi) approach have been applied.

6 Claims, 15 Drawing Sheets

(56) References Cited

OTHER PUBLICATIONS

Figure 2:
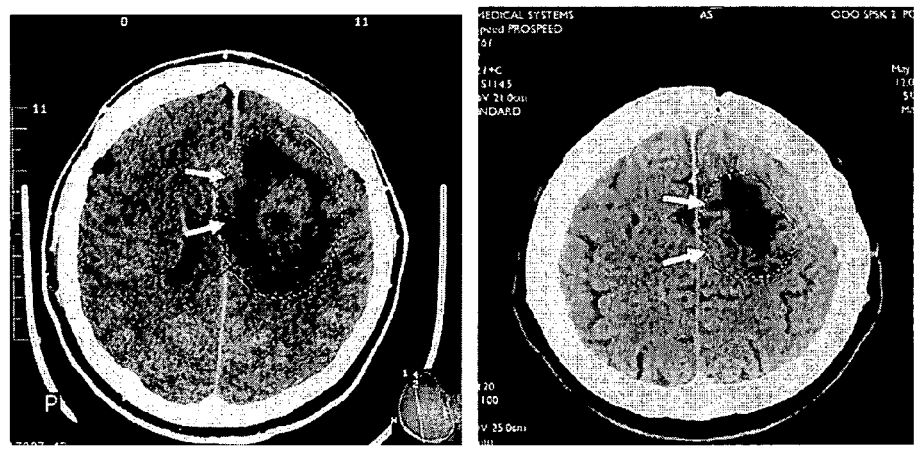

Soutschek, J., et al., "Therapeutic Silencing of an Endogenous Gene by Systemic Administration of Modified siRNAs", Nature 2004; 432:173-8.

Zimmermann, T., et al., "RNAi-Mediated Gene Silencing in Non-Human Primates", Nature, Published online, Mar. 26, 2006.

Partridge, W.M., "Intravenous, Non-Viral RNAi Gene Therapy of Brain Cancer", Expert Opinion on Biological Therapy 2004; 4:1103-13.

Howard, K., "First Parkinson Gene Therapy Trial Launches", Nature Biotechnology 2003; 21:1117-8.

Caplen, N.J., "RNAi Quashes PolyQ", Nature Medicine 2004; 10:775-6.

Fish, R.J., et al., "Short-Term Cytotoxic Effects and Long-Term Instability of RNAi Delivered Using Lentiviral Vectors", BMC Molecular Biology 2004; 5-9.

Gallo, G.L., "Tenascin-C Expression in the Cyst Wall and Fluid of Human Brain Tumors Correlates with Angiogenesis", Neurosurgery 1997; 41:1052-9.

Leung, Ray K.M., et al., "RNA Interference: From Gene Silencing to Gene-Specific Therapeutics", Pharmacology & Therapeutics 2005; 107: 222-39.

Zhang, J., et al., "Single Processing Center Models for Human Dicer and Bacterial RNase III", Cell 2004; 118:57-68.

Parrish, S., et al., "Functional Anatomy of a dsRNA Trigger: Differential Requirement for the Two Trigger Strands in RNA Interference", Molecular Cell 2000; 6:1077-87.

Bhargava, A., et al., "Long Double-Stranded RNA-Mediated RNA Interference as a Tool to Achieve Site-Specific Silencing of Hypothalamic Neuropeptides", Brain Research Protocols 2004; 13:115-25.

Lage, H., "Potential Applications of RNA Interference Technology in the Treatment of Cancer", Future Oncology 2005; 3:103-113.

Kang, C-S., et al., "Suppression of EGRF Expression by Antisense or Small Interference RNA Inhibits U251 Glioma Cell Growth in Vitro and in Vivo", Cancer Gene Therapy 2006; 13:530-538.

Dev, K.K., "Using RNAi in the Clinic", !IDrugs 2006; 9;279-282.

Kumar, P., et al., "Transvascular Delivery of Small Interfering RNA to the Central Nervous System", Nature, 2007, 448, 39-43.

Cantin, E.M., et al., "Molecular Medicine: Entry Granted", Nature, 2007, 448, 33-34.

Daniels, D.A., et al., "A Tenascin-C Aptamer Identified by Tumor Cell SELEX: Systematic Evolution of Ligands by Exponential Enrighment", Proc. Natl. Acad. Sci., USA 2003, 100, 15416-15421.

Fire, A., et al., "Potent and Specific Genetic Interference by Double-Stranded RNA in *Caenorhabditis elegans*", Nature 1998, 391, 806-811.

Brower, V., "RNA Interference Advances to Early-Stage Clinical Trials", JNCI News, Oct. 6, 2010, 1459-1461.

Rolle, K., et al., "Promising Human Brain Tumors Therapy with Interference RNA Intervention (iRNAi)", Cancer Biology & Therapy 9:5, Mar. 1, 2010, 396-406.

\* cited by examiner

CAAGCGACAGAGUGGGGUGAACGCCACCCUGCCAGAAGAGAACCAGCCAGUGGUGUUUAACC
GUUCGCUGUCUCACCCCACUUGCGGUGGGACGGUCUUCUCUUGGUCGGUCACCACAAAUUGG

ACGUUUACAACAUCAAGCUGCCAGUGGGAUCCCAGUGUUCGGUGGAUCUGGAGUCAGCCAGU
UGCAAAUGUUGUAGUUCGACGGUCACCCUAGGGUCACAAGCCACCUAGACCUCAGUCGGUCA

GGGGAGAAAGACCUGGCACCGCCUUCAGAGCCCAGCGAA
CCCCUCUUUCUGGACCGUGGCGGAAGUCUCGGGUCGCUU

Fig. 1

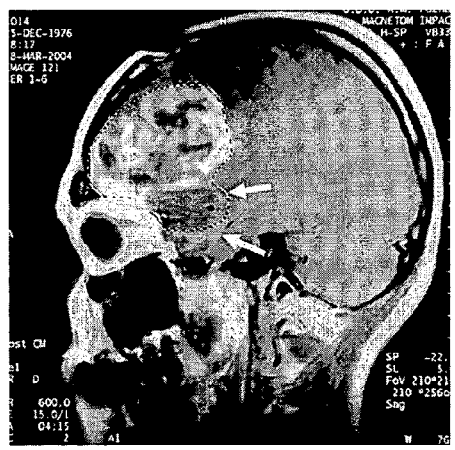 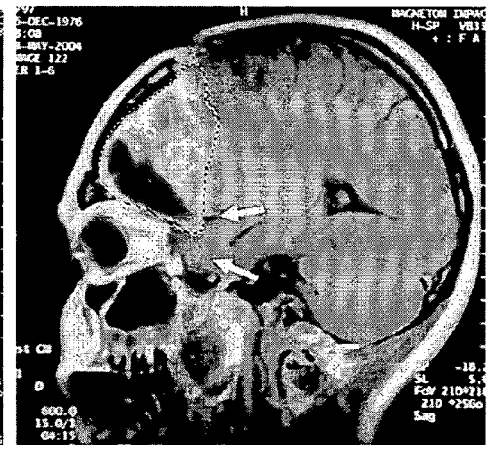
Fig. 3 a)    Fig. 3 b)
Fig. 3

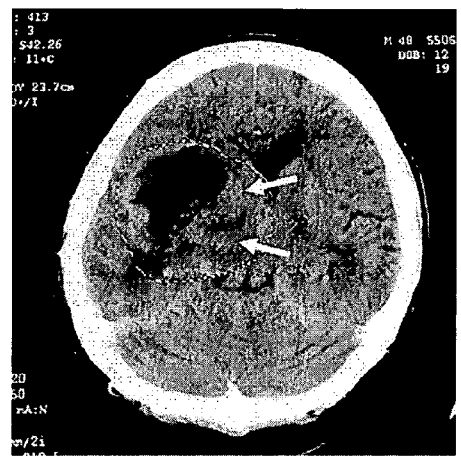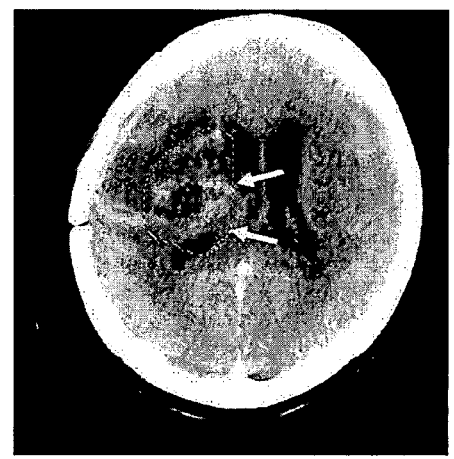
Fig. 4 a)   Fig. 4 b)
Fig. 4

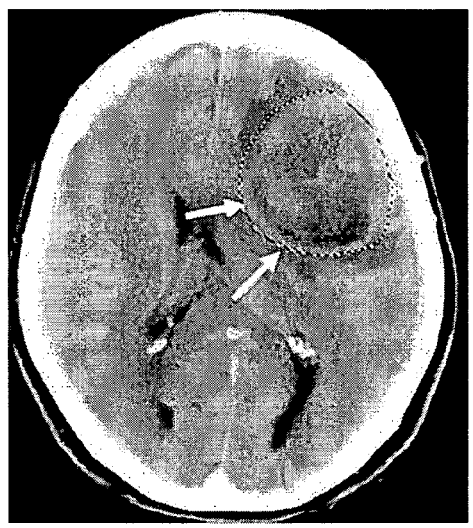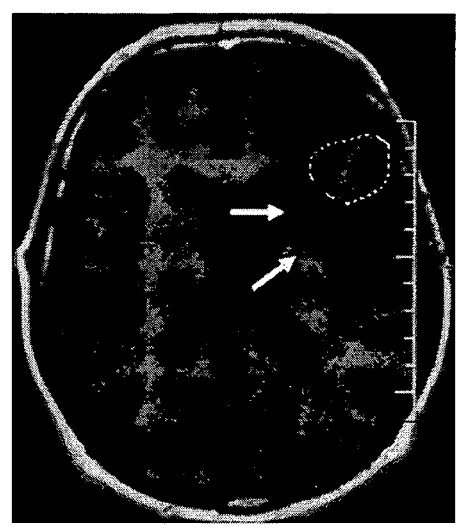
Fig. 5 a)  Fig. 5 b)
Fig. 5

Fig. 6 a)
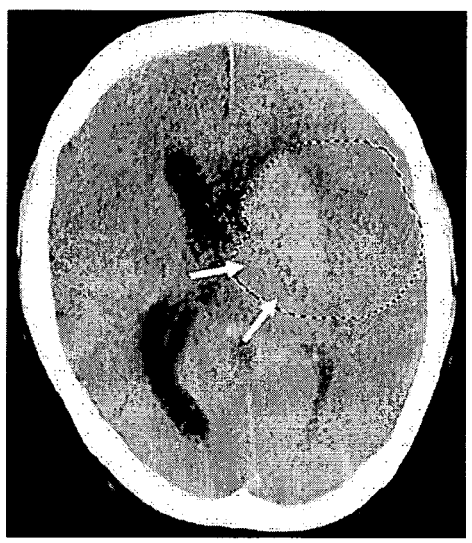
Fig. 6 b)
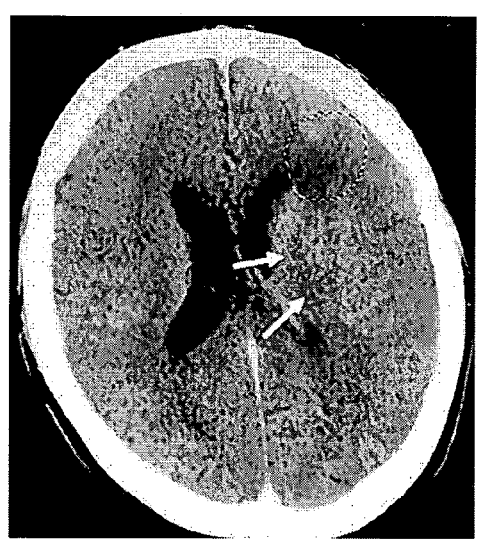
Fig. 6

Fig. 7a
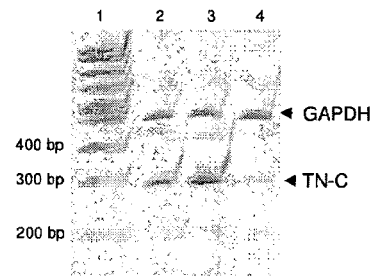
Fig. 7b
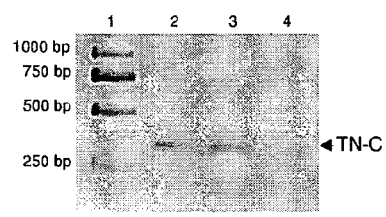
Fig. 7c
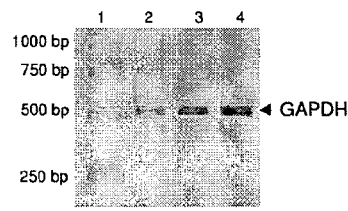
Fig. 7

A
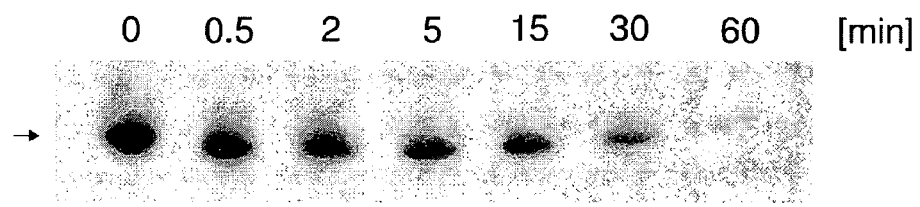
B
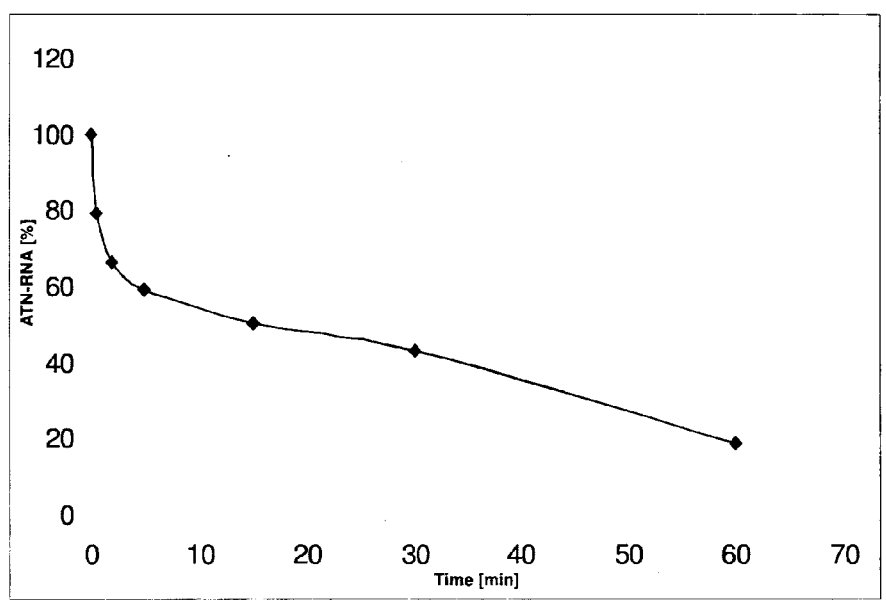
Fig. 8

SEQUENCE LISTING

```
<160> NUMBER OF SEQ ID NOS: 9

<210> SEQ ID NO 1
<211> LENGTH: 326
<212> TYPE: DNA
<213> ORGANISM: Artificial
<220> FEATURE:
<223> OTHER INFORMATION: RNA sequences used in therapy

<400> SEQUENCE: 1
caagcgacag aguggguga  acgccaccu  gccagaagag aaccagccag ugguguuuaa    60
ccguucgcug ucucacccca cuugcggugg gacggucuuc ucuuggucgg ucaccacaaa   120
uuggacguuu acaacaucaa gcugccagug ggaucccagu guucggugga ucuggaguca   180
gccaguugca aauguguag  uucgacgguc acccuagggu cacaagccac cuagaccuca   240
gucggucagg ggagaaagac cuggcaccgc cuucagagcc cagcgaaccc cucuuucugg   300
accguggcgg aagucucggg ucgcuu                                        326

<210> SEQ ID NO 2
<211> LENGTH: 21
<212> TYPE: DNA
<213> ORGANISM: Artificial
<220> FEATURE:
<223> OTHER INFORMATION: siRNA

<400> SEQUENCE: 2
guugcucugg aaaacucaut t                                              21

<210> SEQ ID NO 3
<211> LENGTH: 21
<212> TYPE: DNA
<213> ORGANISM: Artificial
<220> FEATURE:
<223> OTHER INFORMATION: siRNA

<400> SEQUENCE: 3
```

-continued ttcaacgaga ccuuuugagu a                                     21

<210> SEQ ID NO 4
<211> LENGTH: 21
<212> TYPE: DNA
<213> ORGANISM: Artificial
<220> FEATURE:
<223> OTHER INFORMATION: siRNA II

<400> SEQUENCE: 4
uuauugucug guauagugct t                                     21

<210> SEQ ID NO 5
<211> LENGTH: 21
<212> TYPE: DNA
<213> ORGANISM: Artificial
<220> FEATURE:
<223> OTHER INFORMATION: siRNA

<400> SEQUENCE: 5
ttaauaacag accauaucac g                                     21

<210> SEQ ID NO 6
<211> LENGTH: 20
<212> TYPE: DNA
<213> ORGANISM: Artificial
<220> FEATURE:
<223> OTHER INFORMATION: TNC 1

<400> SEQUENCE: 6
agagaaccag ccagtggtgt                                       20

<210> SEQ ID NO 7
<211> LENGTH: 20
<212> TYPE: DNA
<213> ORGANISM: Artificial
<220> FEATURE:
<223> OTHER INFORMATION: TN2

<400> SEQUENCE: 7
gcctgctcct gcagtacatt                                       20

<210> SEQ ID NO 8
<211> LENGTH: 19
<212> TYPE: DNA
<213> ORGANISM: Artificial
<220> FEATURE:
<223> OTHER INFORMATION: GAPDH G1

<400> SEQUENCE: 8
gggtggagcc aaacgggtc                                        19

<210> SEQ ID NO 9
<211> LENGTH: 21
<212> TYPE: DNA
<213> ORGANISM: Artificial
<220> FEATURE:
<223> OTHER INFORMATION: GADPH G2

<400> SEQUENCE: 9
ggagttgctg ttgaagtcgc a                                     21

SEQUENCE OF DSRNA: ATN-RNA SPECIFIC FOR TENASCIN-C

The subject matters of this invention are a sequence of double-stranded RNA: ATN-RNA; intervention using interference RNA (iRNAi); use of a sequence of double-stranded RNA: ATN-RNA; a method of treating a brain tumor and a method of inhibiting a brain tumor cells which express tenascin, a kit for inhibiting cancer cell which expresses tenascin and a method for a kit preparation in a brain tumor therapy. Malignant gliomas preferentially express a number of surface markers that may be exploited as therapeutic targets, including tenascin-C (TN-C), an extracellular matrix glycoprotein that is ubiquitously expressed by malignant gliomas and probably contributes to tumor cell adhesion, invasion, migration and proliferation. For TN-C inhibition, RNA interference intervention (iRNAi) approach have been applied.

It is known that TN-C, the extracellular matrix protein is highly expressed in tumor tissue of the majority of malignant tumors including brain [24,25]. TN-C commonly elevated in high-grade gliomas increases the invasivness of glioma cells. It is the dominant epitope of glioblastoma multiforme [26]. Interestingly, a very high level of matrix metalloproteinase 12 (NMP-12) has been also observed in the high grade glioblastoma multiforme tumors and that TN-C upregulates NMP-12 [27].

In the tumor tissue, TN-C occurs mostly in the extracellular matrix of the fibrotic stoma of highly malignant neoplasms including carcinomas of the colon and breast, fibrosarcomas, lung, melanomas, squamous cell carcinomas, bladder tumor, prostatic adenocarcinoma and along the tumor border [28]. Significantly higher levels of TN-C in homogenates of GBM than in normal brain have been observed.4 The discovery that TN-C presents a dominant epitope in glioblastoma5,6 prompted us to investigate the potential of RNA interference (RNAi) to block the TN-C expression and its effect on the growth of human brain malignancies. The high level of expression of TN-C in human gliomas and astrocytomas correlates with a higher tumor grade and angiogenesis [29, 30].

In the patent application WO2005095622 (published 2005 Oct. 13) c-met siRNA adenovirus vectors inhibit cancer cell growth, invasion and tumorigenicity were described. Suppression of the Hepatocyte growth factor/scatter factor (HGF/SF)-Met signaling pathway by targeting the Met protein tyrosine kinase was tested as strategy for suppressing tumor growth. Using RNA interference (RNAi) technology and adenoviruses carrying siRNA (Ad Met siRNA) target sequences dramatically reduced Met expression in mouse, dog and human tumor cells. Met was suppressed using Ad Met siRNA in mouse mammary tumor (DA3) cells and Met-transformed (NIH3T3 (M114) cells as well as human prostate cancer, sarcoma, glioblastoma, gastric and ovarian cancer cells. Furthermore, the Ad Met siRNA infection reversed transformed cell morphology. Ad Met siRNA killed cancer cells by inducing apoptosis. RNAi targeting Met suppressed HGF/SF-mediated scattering as well as ligand-mediated invasion activity and growth of tumor cells. Met siRNA infection also abrogated downstream Met signaling to molecules such as Akt and p44/42 MAPK. Importantly, the Met siRNA triggered apoptosis was correlated to suppressed tumorigenicity in vivo. Intro-tumoral infection with c-met siRNA adenovirus vectors produced significant reduction in tumor growth. Thus Met RNAi is an effective weapon for targeting Met expression and for treating c-Met<+> cancers.

Despite the described solutions and knowledge concerning the tenascin-C which is highly expressed in the tumor tissues of the majority of malignant tumors including brain tumors, there is still a need to create a new technology where ATN-RNA, a double stranded RNA with a nucleotide sequence homologous to tenascin-C mRNA will be used. There is still a need to create a technology which might be use in the area of neoplastic brain infiltration which cannot be removed surgically, a method in which dsRNA: ATN-RNA is used to suppress human brain tumors through inhibition of the synthesis of tenascin-C with no influence on intracranial pressure-volume relationships and without any local or general inflammatory response.

The goal of the present invention is to apply the interference RNA to block the TN-C expression and its effect on the growth of human brain malignancies, and so to suppress human brain tumors.

The embodiment of such a stated goal and the solution of problems described in the state of the art dealing with treatment and inhibition of tumor cells with the high selectivity of TN-C inhibition with ATN-RNA have been achieved in the present invention.

The subject of the present invention is a sequence of double-stranded RNA: ATN-RNA, characterised in that it contains a fragment of the tenascin-C mRNA sequence at nucleotides 406 to 569 and forms a two-stranded RNA (dsRNA): ATN-RNA with a complimentary RNA sequence, wherein it is over 150 base pairs long.

Preferentially, characterised in that the 100 to 200 nt dsRNA sequence is added and that from this piece any smaller fragments of 20-25 nt may form.

Preferentially, the ATN-RNA sequence causes a decrease in the expression of the gene encoding tenascin-C, retarding tumor growth.

Preferentially, it has been selected from those sequences shown in FIG. 1 (SEQ ID NO 1).

The next subject of invention is an intervention using RNA interference (iRNAi), characterised in that a fragment of tenascin-C mRNA is introduced into a post-operative space wherein the double-stranded RNA (dsRNA): ATN-RNA corresponds to the TN-C mRNA sequence at nucleotide positions 406-569, where the sequence is over 150 nucleotides long, with a complimentary RNA strand.

Preferentially, a sequence selected from among those presented in FIG. 1 is introduced into a post-operative space.

Preferentially, the intervention using RNA interference (iRNAi) consists of the introduction of an RNA sequence containing a fragment of the TN-C mRNA sequence into a post-operative space and encompasses the conjunction of neurosurgical removal of a majority o a tumor with the direct injection of mRNA into the remaining, inoperable tumor cells.

The next subject of invention is the use of a sequence of double-stranded ATN-RNA, containing a fragment of the TN-C mRNA sequence, characterised in that the ATN-RNA corresponds to the TN-C mRNA sequence at nucleotide positions 406-569, where the sequence is over 150 nucleotides long, with a complimentary RNA strand, and is used in the treatment of human brain tumors.

Preferentially, a sequence selected from among those presented in FIG. 1 and is introduced into the resection cavity at the location from which said solid brain tumor was removed.

Preferentially, the ATN-RNA sequence causes a decrease in the expression of the TN-C gene, retarding tumor growth.

Preferentially, it relates to the treatment of human tumors producing tenascin-C.

Preferentially, it relates to brain tumors.

The next subject of invention is a method of treating a brain tumor which expresses tenascin, comprising removing a solid brain tumor expressing tenascin from an afflicted human subject, then forming an enclosed resection cavity at the location from which said solid brain tumor was removed, and then administering to said subject a fragment of the tenascin-C mRNA sequence at nucleotides 406 to 569 and forms a two-stranded RNA (dsRNA): ATN-RNA with a complimentary RNA sequence, wherein it is over 150 base pairs long, that binds to tenascin-C in a therapeutically effective amount.

Preferentially, that, into resection cavity at the location from which solid brain tumor was removed, a sequence selected from among those presented in FIG. 1 is introduced into the resection cavity at the location from which said solid brain tumor was removed. Preferentially, the tumor is a human brain tumors, especially astrocytic brain tumor or Glioblastoma multiforme or Astrocytoma or Anaplastic astrocytoma or Anaplastic oligoastrocytoma or Oligodendroglioma.

Preferentially, administration step is carried out by injection.

Preferentially, a therapeutically effective amount of the sequence is administered in an amount of from 80 to 200 micrograms.

Preferentially, the ATN-RNA sequence causes a decrease in the expression of the tenascin-C gene, retarding tumor growth.

The next subject of invention is a method for inhibiting brain tumor cell which expresses tenascin, comprising removing a solid brain tumor expressing tenascin from an afflicted human subject, then forming an enclosed resection cavity at the location from which said solid brain tumor was removed, and then administering to said subject a fragment of the tenascin-C mRNA sequence at nucleotides 406 to 569 and forms a two-stranded RNA(dsRNA): ATN-RNA with a complimentary RNA sequence, wherein it is over 150 base pairs long, that binds to tenascin-C in a therapeutically effective amount.

Preferentially, that, into resection cavity at the location from which solid brain tumor was removed, a sequence selected from among those presented in FIG. 1 is introduced into the resection cavity at the location from which said solid brain tumor was removed. Preferentially, the tumor is a human brain tumor, especially astrocytic brain tumor or Glioblastoma multiforme or Astrocytoma or Anaplastic astrocytoma or Anaplastic oligoastrocytoma or Oligodendroglioma.

Preferentially, that administration step is carried out by injection.

Preferentially, a therapeutically effective amount of the sequence is administered in an amount of from 80 to 200 micrograms.

Preferentially, the ATN-RNA sequence causes a decrease in the expression of the tenascin-C gene, and inhibition of tumor growth.

Preferentially, the inhibiting cancer cell attachment and growth takes place in the brain.

The next subject of invention is a kit for use in inhibiting cancer cell which expresses tenascin, comprising reagents and components for use in treating a brain tumor, characterised in that it contains a fragment of the tenascin-C mRNA sequence at nucleotides 406 to 569 and forms a two-stranded RNA (dsRNA): ATN-RNA with a complimentary RNA sequence, wherein it is over 100 base pairs long, that binds to tenascin-C in a therapeutically effective amount.

Preferentially, a sequence selected from among those presented in FIG. 1.

Preferentially, the ATN-RNA sequence in the kit causes a decrease in the expression of the tenascin-C gene, and inhibition of tumor growth.

Preferentially, the kit is use for a human brain tumor, especially astrocytic brain tumors or Glioblastoma multiforme or Astrocytoma or Anaplastic astrocytoma or Anaplastic oligoastrocytoma or Oligodendroglioma.

The next subject of invention is a method for a kit preparation, wherein a kit is for use in inhibiting cancer cell which expresses tenascin, characterised in that, ATN-RNA is prepared by transcription of ATN-DNA with T7/T3 polymerases and is delivered directly into surgically created resection cavity of patients with malignant brain tumor, and wherein a plasmid harboring TN-C DNA is cleaved with HindIII or EcoRI, and ATN-RNA is synthesized in vitro with T7 and T3 RNA polimerases, and where a total RNA from brain, ovary and intestine tumor tissues is isolated and a reverse transcription is carried out and than the resultant cDNA is amplified with primers complementary to the tenascin-C and glyceraldehyde-3-phosphate dehydrogenase, GAPDH as an internal control in PCR reaction.

Preferentially, two strands of RNA are prepared separately and labeled with [$^{32}$P-γ]ATP and T4 RNA kinase at 37° C. during 45 min, than after annealing and renaturation (50 mM Tris-HCl pH 7.5, 50 mM NaCl, 95° C. for 3 min, 75° C. for 30 min and slow cooling down for 4 hrs to 25° C.) and stability of radiolabeled dsRNA ($2 \times 10^4$ cpm/reaction) is determined in 90-μl human brain tumor extract, which is obtained by homogenization of the tissue in 10 mM Tris-HCl buffer pH 7.5, sonication (3×15 sec.) and elimination of debris by centrifugation at 13 000 rpm for 3 min and where a reaction mixture is incubated at 25° C., and 10 μl portions is removed at specific times, than reactions are stopped by the addition of loading solution (30% glycerol, 0.25% bromophenol blue, 0.25% xylene cyanol, 1×TEB) and freezing in liquid nitrogen, and next analyzed by electrophoresis on 10% poliacrylamide gel with 7 M urea, the radiolabeled dsRNA is detected and quantified by phosphorimager analysis.

Preferentially, the resultant cDNA is amplified with primers complementary to the tenascin-C (TN1: AGAGAAC-CAGCCAGTGGTGT (SEQ ID NO 6), TN2: GCCTGCTC-CTGCAGTACATT (SEQ ID NO 7)) and glyceraldehyde-3-phosphate dehydrogenase, GAPDH (G1: GGGTGGAGCCAAACGGGTC (SEQ ID NO 8), G2: GGAGTTGCTGTTGAAGTCGCA (SEQ ID NO 9)) as an internal control in PCR reaction, where the PCR reaction was initiated with denaturation at 94° C. for 2 min, annealing at 55 for 1 min, extension at 72 for 30 sec, followed by 30 cycles and equal volumes of amplified products are electrophoresed on 1.5% agarose gel and stained with ethidium bromide.

The attached figures facilitate a better understanding of the nature of the present invention.

FIG. 1 presents RNA sequences used in therapy—ATN-RNA the double stranded RNA (dsRNA) fragment matching N-C mRNA in nucleotide positions 406-569 (SEQ ID NO 1).

FIG. 2 presents a computer tomography image (CT) of human brain tumor marked with dashed line (male, W.F., 53 yrs), (A) before surgery, tumor in the fronto-parietal region (glioblastoma multiforme) and (B) Four weeks later, total tumor resection and ischemic changes. Arrows point to the sites of ATN-RNA application.

FIG. 3 presents Magnetic Resonance Image (MRI) of human brain tumor circled with dashed line (female, D.M., 28 yrs), (A) before surgery, tumor in the fronto-temporal region (glioblastoma multiforme) penetrating to the middle brain area and (B) Eight weeks after, the recurrence of tumor mainly in the different sites of ATN-RNA application. Arrows point the sites of ATN-RNA injection.

FIG. 4 presents a computer tomography image (CT) of human brain tumor marked with dashed line (male, O.A., 49 yrs), (A) before surgery, tumor in the parieto-temporal region penetrating to the middle brain area (glioblastoma multiforme) and (B) five weeks after, the recurrence of tumor, ischemic changes and brain oedema. Arrows point the sites of ATN-RNA application.

FIG. 5 presents computer tomography, CT (A) and magnetic resonance imaging, MRI (B) images of patient (male, G.L., 46 yrs) with human brain glioblastoma multiforme. CT (A) shows GBM before surgery in the left fronto-parietal region penetrating to the central area (dotted line). MRI (B) recorded 12 weeks after surgery shows the recurrence of tumor in the remote distance from the sites of ATN-RNA application. Arrows point the sites of ATN-RNA injection.

FIG. 6 presents computer tomography (CT) images of diffuse astrocytoma WHO II in patient (male, K.M., 32 yrs) before (A) and after (B) surgery. Panel (a) displays brain glioma with a significant space-occupying effect and ventricular system displacement in the left fronto-parietal region (dotted line). Panel (B) displays CT 10 weeks after tumor resection and ATN-RNA application. It demonstrates recession of the space-occupying effect and postoperative ischemic changes (dotted line). Astrocytoma area disappeared around sites of ATN-RNA injection.

FIG. 7 presents RT-PCR analysis of the RNA isolated from human glioblastoma tissues and cultured ex vivo GBM cells transfected with ATN-RNA. cDNA was amplified using primers complementary to the TN-C (300 bp fragment DNA) and GAPDH (500 bp fragment DNA) as an internal controls.

(a) The PCR products were separated with 6% PAGE with 7 M urea followed by ethidium bromide staining. Lane 1: molecular mass marker. RT-PCR reaction was done with RNA isolated from border line (lane 2), and central part of GBM tissue (lane 3), cultured GBM cells transfected with ATN-RNA (lane 4).

(b) Agarose (1.5%) analysis of TN-C PCR products stained with ethidium bromide of ex vivo GBM cells transfected with scrambled siRNAs (control) and ATN-RNA. Lane 1: molecular mass marker. RT-PCR reaction was done with RNA isolated from nontransfected GBM cells (lane 2), transfected GBM cells with scrambled siRNAs (lane 3) and GBM cells transfected with ATN-RNA (lane 4).

(c) Agarose (1.5%) analysis of GAPDH PCR products stained with ethidium bromide of ex vivo GBM cells transfected with scrambled siRNAs (control) and ATN-RNA. Lane 1: molecular mass marker. RT-PCR reaction was done with RNA isolated from nontransfected GBM cells (lane 2), transfected GBM cells with scrambled siRNAs (lane 3) and GBM cells transfected with ATN-RNA (lane 4).

FIG. 8 presents time dependent stability of ATN-RNA in GBM tissue extract. A. The autoradiogram of 10% polyacrylamide gel electophoresis with 7 M urea of $^{32}$P-labeled ATN-RNA incubated in human brain tumor (GBM) extract at 25° C. at different time.

Quantification of dsRNA was estimated using phosphorimager analysis (ImageQuant). Remaining, nondegraded ATN-RNA is expressed in percents. B. Remaining amounts of ATN-RNA after incubation in GBM extract as a function of treatment time.

Figure 9:
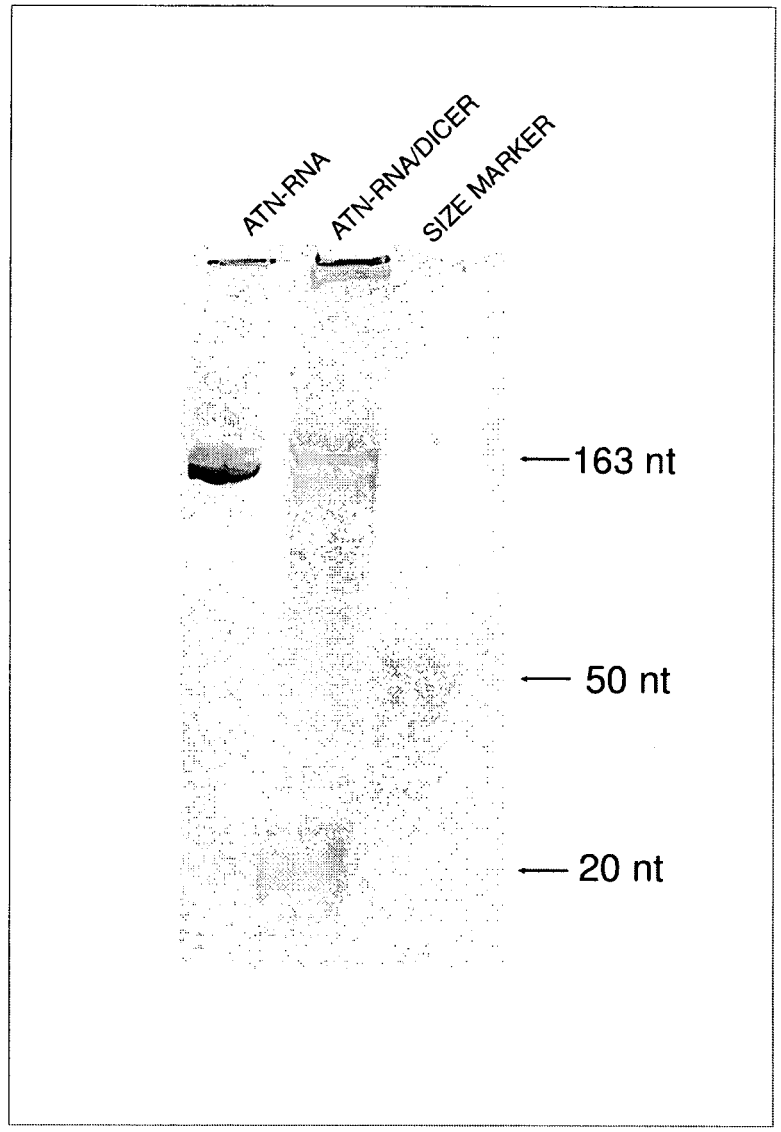

FIG. 9 presents an analysis of $^{32}$P-labeled ATN-RNA (163 bp) hydrolyzed products with human DICER on 10% polyacrylamide gel electophoresis with 7 M urea. Among of various RNA fragments a fraction of 20 nt oligonucleotide is visible.

Figure 10:
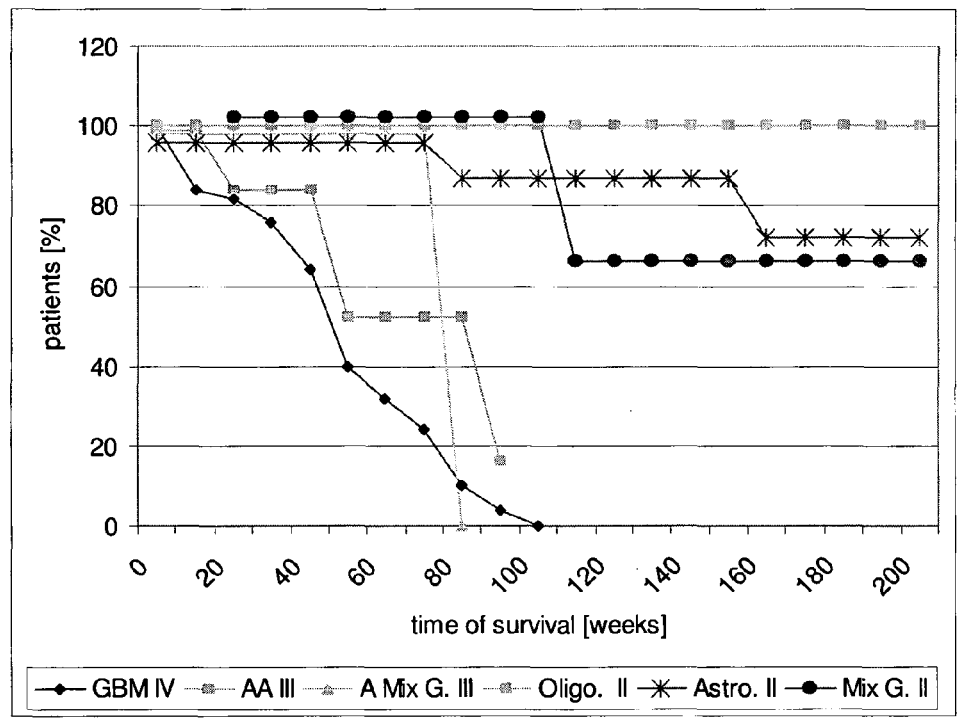

FIG. 10 presents a graph demonstrating differences in survival times according to histopathology diagnosis.

Figure 11:
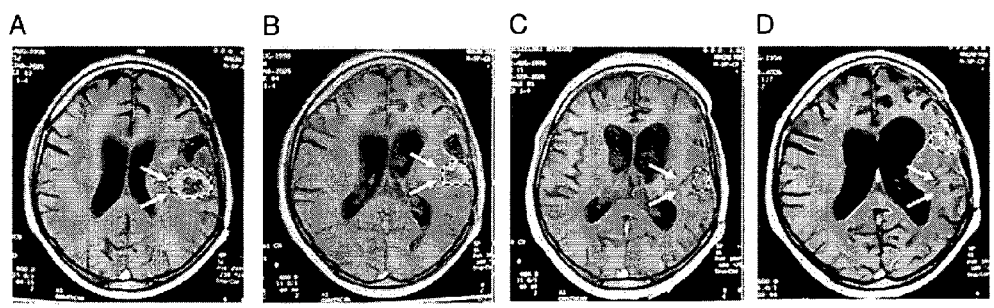

FIG. 11 presents a magnetic resonance images (MRI) of recurrent glioma mixtum oligo-astrocytoma (WHO II) of patient C.R. (male, 48 yrs) in fronto-parietal region A—recurrent tumor after 32 weeks (circled with dotted line) after first surgery. B—4 weeks after reoperation, there is no tumor tissue recurrence visible. Dotted line indicate postsurgical ischemic area. C—28 weeks after reoperation, without signs of tumor recurrence. D—56 weeks after operation. Ischemic postsurgical area is marked (dotted line). Dotted line points) before reoperation. B—8 weeks after reoperation. Dotted line identifies postsurgical ischemic area, C—40 and D—72 weeks after surgery. No tumor relapse is visible. Application recurrence of glioma. Arrows indicate site of ATN-RNA injection.

Figure 12:
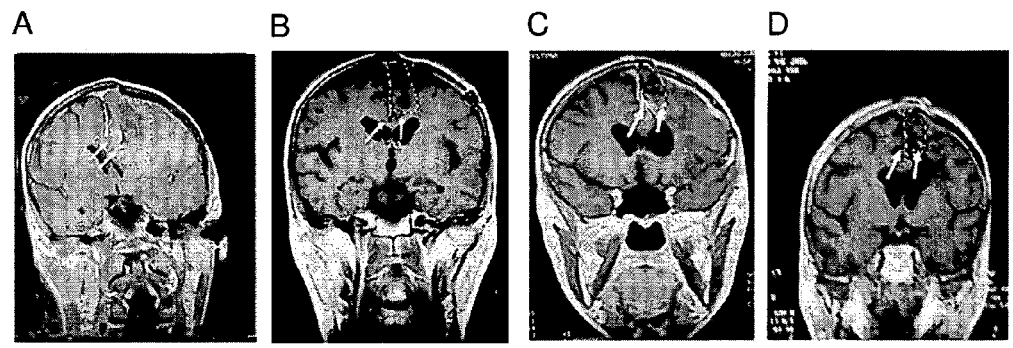

FIG. 12 presents magnetic resonance images (MRI) of tumor cerebri recidivans oligodendroglioma (WHO II) of patient T.K. (female, 53 yrs) 5 yrs after first surgery. A-tumor infiltraties to corpus callosum (dotted line) before reoperation. B—8 weeks after reoperation. Dotted line identifies postsurgical ischemic area, C—40 and D—72 weeks after surgery. No tumor relapse is visible. Application of ATN RNA designated by arrows.

Figure 13:
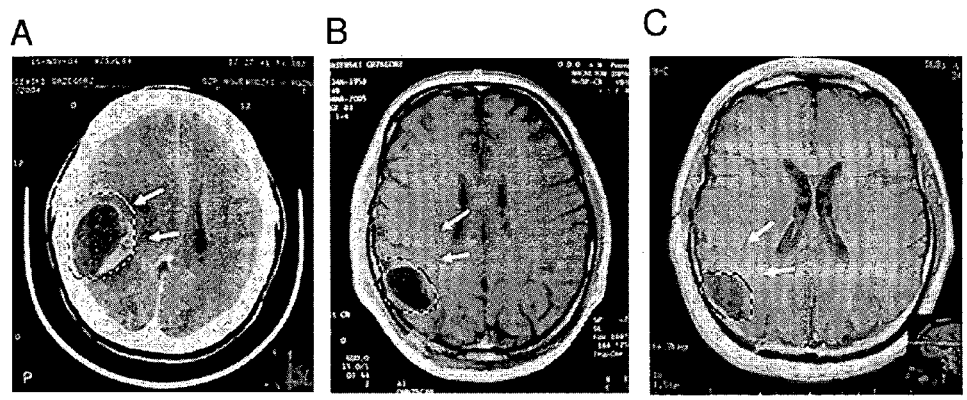
Figure 14:
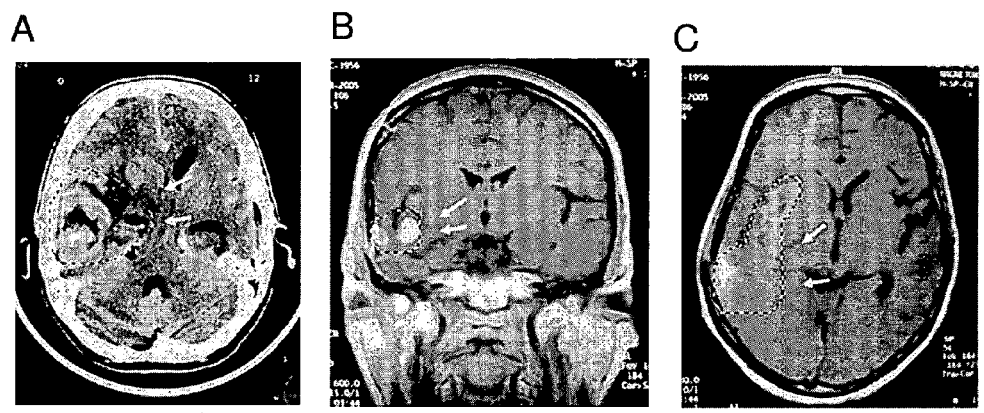

FIG. 13 presents CT and MR images of glioblastoma multiforme (WHO IV) of patient W.G. (male, 46 yrs) A—CT demonstrates cerebral tumor in right tenporo-parietal region (dotted line). Displacement of midline structures toward opposite hemisphere is effected by increased intracranial pressure. B—MRI 16 weeks after tumor removal (dotted line), C—MRI done 64 weeks after operation. There are no signs of GBM recurrence. Arrows identify a region of ATN RNA application FIG. 14 presents CT and MR images of glioblastoma multiforme (WHO IV) of patient W.D. (male, 48 yrs). A—CT demonstrates cerebral tumor in right temporal region (dotted line) and ventricular system displacement towards left hemisphere and brain edema, B—MRI done 16 weeks after subtotal tumor removal presents local tumor recurrence close to sites of ATN RNA injection. There are not displacement of midline structures and ventricular system, C—MRI 36 weeks after operation reveals tumor recurrence in temporal region. Ventricular system is not displaced but slight compression in cerebral right hemisphere is observed. Arrows point to the sites of ATN RNA injection.

Figure 15:
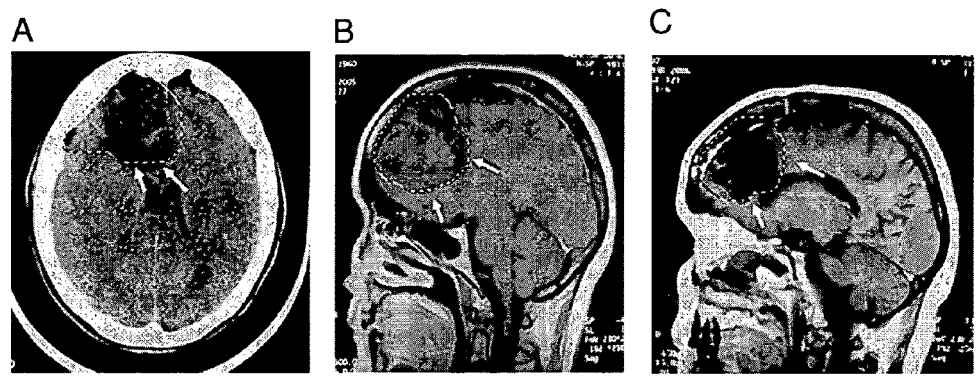

FIG. 15 presents CT (A) and MR (B, C) images of anaplastic astrocytoma (WHO) III of patient K.B. (male, 44 yrs). A—CT before surgery demonstrates cerebral in right frontal region infiltrating the left frontal lobe (dotted line) and brain edema, B—MRI picture (in sagittal projection) shows left frontal tumor penetrating into the central region (dotted line), C—MRI 40 weeks after surgery demonstrates cerebral changes after complete tumor resection (dotted line). There is no tumor recurrence. Arrows indicate site of ATN RNA injection.

Below, there are example embodiments of the present invention defined above.

EXAMPLES

RNA Preparation

ATN-RNA was prepared by transcription of ATN-DNA with T7 polymerase and delivered directly into surgically created resection cavity of patients with malignant brain tumor.

Plasmid harboring TN-C DNA was cleaved with HindIII or EcoRI. ATN-RNA was synthesized in vitro with T7 and T3 RNA polimerases. Two strands of RNA were prepared separately. For stability experiment T7 RNA strand was labeled with [$^{32}$P-γ]ATP and T4 RNA kinase at 37° C. during 45 min. After annealing and renaturation (50 mM Tris-HCl pH 7.5, 50 mM NaCl, 95° C. for 3 min, 75° C. for 30 min and slow cooling down for 4 hrs to 25° C.). Stability of radiolabeled dsRNA ($2 \times 10^4$ cm/reaction) was determined in 90-μl human brain tumor extract. The extract was obtained by homogenization of the tissue in 10 mM Tris-HCl buffer pH 7.5, sonication (3×15 sec.) and elimination of debris by centrifugation at 13 000 rpm for 3 min. Reaction mixture was incubated at 25° C., and 10 μl portions were removed at specific times. Reactions were stopped by the addition of loading solution (30% glycerol, 0.25% bromophenol blue, 0.25% xylene cyanol, 1×TEB) and freezing in liquid nitrogen, and next analyzed by electrophoresis on 10% poliacrylamide gel with 7 M urea. The radiolabeled dsRNA was detected and quantified by phosphorimager analysis (Molecular Dynamics, Sunnyvale, Calif.) [FIGS. 8 and 9].

Inhibition of Tenascin-C in GBM Cultured Cells

For transfection and gene silencing assays ex vivo brain tumor tissue (fragmented) was resuspended in medium and transferred to 6-well plates. Cells were cultured in DMEM (GIBCO BRL) supplemented with 10% FCS, penicillin (100 μg/ml) and streptomycin (100 μg/ml) (Invitrogen).

The cells at 50% confluence were transfected in presence of oligofectamine (Invitrogen) with ATN-RNA and two control scrambled siRNAs: siRNA (I: sense strand-5'GUUGCU-CUG GAAAACUCAUTT3' (SEQ ID NO 2), antisense strand 3'TTCAACGAGACCUUUUGAGUA5' (SEQ ID NO 3); and II: sense strand-5'UUAUUGUCUGG UAUAGUGCTT3' (SEQ ID NO 4), antisense strand-3'TTAAUAACAGAC-CAUAUCACG5' (SEQ ID NO 5)). After next 24 hours cells were harvested for RNA isolation. RT-PCR analysis was carried out.

RNA Isolation and RT PCR Analysis

Total RNA from brain, ovary and intestine tumor tissues, was isolated with Ambion kit. Reverse transcription was carried out using: 2 μg RNA, random primer and RevertAid™ H Minus M-MuLV reverse transcriptase (Fermentas) according to the manufactures instructions. The resultant cDNA was amplified with primers complementary to the tenascin-C (TN1: AGAGAACCAGCCAGTGGTGT (SEQ ID NO 6), TN2: GCCTGCTCCTGCAGTACATT (SEQ ID NO 7)) and glyceraldehyde-3-phosphate dehydrogenase, GAPDH (G1: GGGTGGAGCCAAACGGGTC(SEQ ID NO 8), G2: GGAGTTGCTGTTGAAGTCGCA (SEQ ID NO 9)) as an internal control in PCR reaction. PCR reaction was initiated with denaturation at 94° C. for 2 min, annealing at 55 for 1 min, extension at 72 for 30 sec, followed by 30 cycles. Equal volumes of amplified products were electrophoresed on 1.5% agarose gel and stained with ethidium bromide.

Stability ATN-RNA In Vitro

Plasmid harboring TN-C DNA was cleaved with HindIII or EcoRI. ATN-RNA was synthesized in vitro with T7 and T3 RNA polymerases. Two strands of RNA were prepared separately [1]. T7 RNA strand was labeled with [$^{32}$P-γ]ATP and T4 RNA kinase at 37° C. for 45 min. After annealing of both RNA strands (labeled and unlabeled) stability of radiolabeled dsRNA ($2 \times 10^4$ cpm/assay) was determined in 90-μl human brain tumor extract, which was obtained by homogenization of the 100 mg fragment tissue in 1 ml 10 mM Tris-HCl buffer pH 7.5, sanitation (3×15 sec.) and elimination of debris by centrifugation at 13 000 rpm for 3 min. Reaction mixture (90 ul) was incubated at 25° C., and 10-μl portions were removed at specific period of times. Reaction was stopped by the addition of loading solution (30% glycerol, 0.25% bromophenol blue, 0.25% xylene cyanol) and freezing in liquid nitrogen, and analyzed by electrophoresis on 10% polyacrylamide gel with 7 M urea. The [$^{32}$P] dsRNA was detected and quantified by phosphorimager analysis (Image Quant).

In many neoplasma up regulation of certain growth factors or their receptors or the deregulation of intracellular signal transduction pathways, represents key elements in the process of malignant transformation and progression of normal cells towards tumor cells leading to uncontrolled proliferation and decreased apoptosis. Altered expression levels of certain genes play a pivotal role in several pathological conditions. Malignant gliomas selectively express factors that are not present on normal CNS tissue among them tenascin-C (TN-C). TN-C is expressed ubiquitously in high-grade gliomas but not in normal brain. It is a large, extracellular matrix glycoprotein expressed at various stages of differentiation. The level of TN-C correlates well with tumorigenesis-enhancing processes and supports malignant transformation, uncontrolled proliferation, metastasis, angiogenesis and escaping from tumor immunosurveilance [32].

Increase in total TN-C could activate cell proliferation by direct binding and activation of the epidermal growth factor receptor by the epidermal growth factor receptor-like repeats of TN-C. It is involved in cell-extracellular matrix interactions, which are key determinant in tumorigenesis, characterized by numerous tumor stroma interactions.

TN-C and its splice variants expression correlate with increased cell migration, tissue remodeling, angiogenesis and local infiltration of normal tissues by tumor cells of various carcinomas. There is one of the main reasons why the outcome for primary central nervous system tumors, including glioblastoma multiforme (GBM), the most common and deadliest primary, adult malignant brain tumor, remains unacceptable. As the failure of treatment is usually due to insufficient local control of the site of surgical resection, novel local therapies are still necessary. Development of more effective alternative treatments will be crucial to improve the survival of patients with these tumors. As most malignant gliomas are well known to be chemo- and radio-resistant due to the inhibition of an apoptotic pathway, RNA interference (RNAi) may be suitable for their treatment.

RNAi is a sequence specific, conserved pathway in which double stranded RNA molecules (dsRNA) have been identified as a mediator of functional gene silencing of specific genes in variety eukaryotic organisms [33]. dsRNAs are processed into small RNAs of 20-30 nucleotides in length by the ribonuclease III (RNase III) enzyme Dicer.

The small RNAs are the specificity determinants of the pathway, assembling into the RNA-induced silencing complex (RISC), the multiprotein entity that is guided to complementary RNA, resulting in silencing of the message.

Interestingly, RNAi is not a gene therapy because it involves the insertion of genes into an individual's cells, which then produce a protein to treat a disease. The disadvantage with gene therapy is that it is difficult to determine when the gene stops producing the protein. RNAi therapy, however, is the injection of a controlled amount of RNA. ATN-RNA is a RNA drug that is similar to a natural product found in the human body, and since is a RNA it is highly unlikely to cause an allergic or immunogenic reaction in patients.

To down regulation of TN-C in brain tumor, we have applied interference RNA intervention (iRNAi). RNA interference intervention (iRNAi) with ATN-RNA is a promising local adjuvant therapy after surgery for patients with malignant gliomas. It involves the direct delivery into the tumor tissue resected area the therapeutical dsRNA which induces RNA interference effects downstream of application site and specifically down regulates synthesis of TN-C. This is the site directed therapy which may improve local control and overall outcome for malignant glioma patients. Locally administered therapy offers the ability to achieve a greater effective concentration in the tumor vanity by bypassing the blood-brain barrier while limiting potential systemic exposure to drug degradation. Therefore invasive tumor cells that have migrated beyond the penetration by another regionally administered therapeutics as biodegradable wafers or monoclonal antibodies, can be treated effectively with iRNAi.

The dsRNA matching TN-C mRNA, called ATN-RNA, was prepared (FIG. 1). It is assumed that human DICER 13 [17] will bind and cleave ATN-RNA into 21-25 nucleotide dsRNA species, which, as a part of RISC machinery, can target many sites of mRNA and multiply of mRNA silencing effect. The selected sequence of dsRNA is short enough to evade adverse effects and long enough to be a good source of short interference RNAs (siRNA). It has been suggested that over 200-fold more siRNA is required to achieve the effects similar to those of dsRNA [18, 19, 31].

In these studies we use double stranded interfering RNAs (dsRNAs) to reduce tenascin-C expression in brain tumor cells. RNAi was injected into postoperative area of 48 patients. The follow up study with MRI and CT clearly show increased survival at better quality of life. The technology is called intervention with RNAi (iRNAi) (Table 1).

We have prepared dsRNA (ATN-RNA) ca 160 nt with the sequence complementary to TN-C and showed sequence specificity in vitro and ex vivo towards TN-C mRNA. ATN-RNA has been applied in 48 patients after resection of brain tumor.

TABLE 1

Patients with brain tumors (Grade II-IV) after resection and treatment with ATN-RNA.

| No. of patients | Patient name | Sex | Age (yrs) | Glioma grade | Brain tumor location | Tumor area (mm) |
|---|---|---|---|---|---|---|
| 1 | DM | F | 28 | IV | fronto-temporal/corpus callosum infiltration | Φ 70 |
| 2 | WJ | F | 62 | IV | fronto-parietal | 46 × 40 |
| 3 | WF | M | 53 | IV | fronto-parietal | 47 × 36 |
| 4 | SM | M | 54 | IV | temporal | 75 × 50 |
| 5 | GE | F | 48 | IV | fronto-parieto-temporal | 73 × 52 |
| 6 | OA | M | 49 | IV | parieto-temporal/corpus callosum infiltration | 56 × 54 |
| 7 | GL | M | 46 | IV | frontal | 60 × 50 |
| 8 | KM | M | 32 | II | fronto-parieto-temporal | 78 × 64 |
| 9 | CZ | F | 53 | IIIR | frontal | 43 × 44 |
| 10 | JR | M | 36 | AF II | fronto-parieto-temporal | 80 × 56 |
| 11 | TK | F | 52 | ODG II | frontal/corpus callosum infiltration | 72 × 44 |
| 12 | RJ | M | 60 | IV | frontal | 60 × 40 |
| 13 | ZM | M | 47 | III | parietal | 70 × 50 |
| 14 | MJ | M | 67 | IV | fronto-temporal | 55 × 60 |
| 15 | KM | F | 49 | III/IV | frontal | 60 × 45 |
| 16 | BZ | M | 53 | IIAF | frontal/corpus callosum infiltration | 60 × 70 |
| 17 | WK | F | 69 | IIIAA | parietal/corpus callosum infiltration | 34 × 25 |
| 18 | WG | M | 46 | IV | parieto-temporal | 57 × 47 × 50 |
| 19 | WD | F | 48 | IV | temporal | 50 × 40 |
| 20 | PS | F | 43 | II | fronto-parieto-temporal | 100 × 80 × 80 |
| 21 | KJ | F | 70 | IV | parietal | 50 × 42 |
| 22 | JB | F | 48 | IV | fronto-parietal | 67 × 69 × 62 |
| 23* | CW | M | 49 | IIIR/IV | fronto-parietal | Φ 70 |
| 24 | CR | M | 48 | II | fronto-parietal | 80 × 50 |
| 25 | BM | M | 75 | IV | fronto-parieto-temporal | 71 × 46 × 64 |
| 26 | DM | F | 55 | IV | parieto-temporal | 50 × 50 × 60 |
| 27* | SM | M | 54 | IV | frontal | 60 × 40 × 50 |
| 28 | RK | M | 45 | IV | parieto-temporal | 70 × 50 × 40 |
| 29 | TZ | M | 49 | IV | fronto-parieto-temporal | 90 × 50 × 60 |
| 30 | WK | M | 54 | IV | frontal | 75 × 50 |
| 31 | KB | F | 44 | III | frontal | 50 × 60 |
| 32 | JS | M | 37 | ARIII | frontal | 80 × 50 |
| 33 | HJ | M | 65 | IV | frontal | 60 × 30 × 70 |
| 34 | DA | F | 40 | Meningeoma II | parieto-temporal | 50 × 40 |
| 35* | KJ | M | 66 | IV | fronto-temporal | 60 × 40 |
| 36 | KB | M | 55 | IV | frontal | 50 × 40 |
| 37 | LD | F | 40 | IIIR | fronto-temporal | 70 × 40 |
| 38 | ST | F | 63 | IIIR | frontal | 80 × 60 × 50 |
| 39 | JT | F | 59 | IV | corpus callosum infiltration | 40 × 50 × 30 |
| 40 | BK | F | 54 | III | parietal | 55 × 40 × 55 |
| 41 | PH | F | 35 | IIIAA | fronto-parietal | 60 × 40 × 40 |
| 42* | KA | M | 59 | IV | parieto-occipit | 50 × 40 × 40 |
| 43 | KE | F | 54 | IV | temporal | Φ 55 |
| 44 | ND | F | 61 | IVR | frontal | Φ 40 |
| 45 | TT | M | 58 | IVR | frontal/corpus callosum infiltration | 72 × 66 × 50 |
| 46 | GL | M | 51 | IV | frontal | 69 × 56 × 65 |
| 47 | LB | M | 64 | IV | frontal | 85 × 50 × 65 |
| 48 | LL | M | 29 | III | parietal | 80 × 50 × 50 |

Patients 23, 27, 35 and 42 (marked with *) were treated twice with ATN-RNA after next surgery.
AA—Astrocytoma Anaplasticum,
AF—Astrocytoma fibrylare,
ODG—oligodendrioglioma,
R—recurrence

TABLE 2

Number of patients with various forms of primary and recurrent brain tumors treated using ATN RNA.

| Brain tumor | WHO grade | No. of patients treated with ATN-RNA | |
|---|---|---|---|
| | | Primary tumor | Recurrent tumor |
| Glioblastoma muliforme | IV | 15 | 10 |
| Anaplastic astrocytoma | III | 3 | 3 |
| Oligodendroglioma | II | — | 3 |
| Mixed oligo-astrocytoma | II | — | 3 |
| Anaplastic oligo-astrocytoma | III | — | 1 |
| Astrocytoma | II | 2 | 6 |

TABLE 3

Median survival (weeks) of 46 patients with brain tumor treated with ATN RNA.

| Brain tumor | WHO grade | No. of patients | Patients (%) | median survival (weeks) | Range of median survival (weeks) |
|---|---|---|---|---|---|
| Glioblastoma muliforme | IV | 25/17* | 54.3 | 55.3 | 7-104 |
| Anaplastic astrocytoma | III | 6/5* | 13.1 | 74.8 | 23-93 |
| Anaplastic oligo-astrocytoma | III | 1/1* | 2.2 | 80 | 80 |
| Oligodendroglioma | II | 3/2* | 6.5 | 312 | 260-364 |
| Low-grade astrocytoma | II | 8/4* | 17.4 | 236 | 85-471 |
| Mixed oligo-astrocytoma | II | 3/1* | 6.5 | 159 | 159 |

*number of questionnaires

Efficacy of ATN-RNA treatment was estimated on the basis of follow-up studies including general and neurological condition as well as neuroimaging studies with the CT and MRI measured for each month periods after the treatment. The consent for the treatment was obtained from patients.

In case: male, 53 years old (No. 3 in Table 1), the glioma recurrence after ATN-RNA treatment was not observed (FIG. 2). CT image before surgery (FIG. 2A) demonstrates neoplastic process in the fronto-parietal region (GBM). Four weeks later it shows entire mass tumor resection and postoperative ischemic changes (FIG. 2B). The follow-up examination reveals that patient to be in a good condition. There was no tumor reccurrence up to 14 months after surgery. In the other two cases (No. 1 in Table 1: female, 28 years old, FIG. 3 and No. 6 in Table 1: male, 49 years old, FIG. 4), the results are slightly different. MRI of the recurrent glioma before surgery displays tumor (GBM) in the fronto-temporal region penetrating to the central area (FIG. 3A), but two months after the ATN-RNA treatment a recurrence of tumor is visible only in the remote sites of ATN-RNA application (FIG. 3B). A similar CT picture was obtained for case No. 6 in Table 1: GBM in the parieto-temporal region penetrating to the central area (FIG. 4A). Five weeks after the operation the remote tumor recurrence, ischemic changes and restricted brain oedema were observed (FIG. 4B). For both these cases, clear differences in focal and distant sites of the operation area are visible. Nearby the injection spots marked with arrows there is no evidence for a tumor recurrence. Its growth was completely inhibited. However a relapse of the neoplasm in distal sites from the ATN-RNA injection sites in the postoperative cavity can be noticed. However, the relapse of GBM after ATN RNA treatment is much slower as compared with the patients not treated with dsRNA and the survival time is longer in these cases. A very similar effect of ATN-RNA was observed for the case: male, 46 years old (No. 7 in Table 1).

Clearly GBM is missing in the venue of ATN-RNA injection, but some recurrence is observed in the remote area (FIG. 5). The hemiparesis is seen as it was before the surgery. The patient was in good condition. The most spectacular result was obtained for patient in case: male, 32 years old, (No. 8 in Table 1) with diffuse astrocytoma (WHO II). It is known that more than 70% of grade II tumors transform into grade III and IV within 5-10 year time. In that case astrocytoma infiltrates right cerebral hemisphere and penetrates to the central area (FIG. 6). The infiltrative nature of that tumor does not allow a surgical action even in areas where wide resection is possible. CT image shows brain glioma with a significant space-occupying effect and a ventricular system displacement in the fronto-parietal region is seen (FIG. 6A). Ten weeks after ATN-RNA application, CT image demonstrates almost total recession of the space-occupying effect, disappearance of the glioma in the area of ATN-RNA injection. MRI 18 months beyond surgery did not show tumor recurrence. (FIG. 6B). Neurologic deficits were not Observed [31].

The specific effect of ATN-RNA can be seen from inspection of (FIG. 12). Patient TK, female, 53 years old (No. 11 in Table 1) was diagnosed with tumor cerebri recidivans lobi frontalis (FIG. 12A). Only a subtotal resection of a tumor was carried out because it infiltrated ed to corpus callosum. Therefore ATN-RNA was injected directly to the remaining part of tumor (see arrows on FIG. 12). MRI image eight weeks after surgery showed no recurrence of neoplasm in the area occupied before surgery with tumor. That patient was in good condition [31].

TABLE 4

A comparison of median survival of patients with surgically resected Grade II-IV brain tumors.
Patients were treated either with ATN-RNA or brachytherapy.
The table was completed for 23 patients

| Tumor grade | Median survival (weeks) | |
|---|---|---|
| | ATN-RNA | brachytherapy |
| 20-40 yrs | | |
| Glioma/II | 180.0 | 176.3 |
| 41-60 yrs | | |
| Glioma/II | 178.0 | 176.0 |
| NonGBM/III | 72.3 | 59.0 |
| GBM/IV | 66.7 | 52.8 |

To proof the specificity of ATN-RNA action on tenascin-C mRNA of human brain tumor, we analysed expression of native TN-C mRNA in GBM cells using RT-PCR approach (FIG. 7). One can see different amount of the tenascin mRNA PCR products at two sites of glioblastoma tissue and at the same time the constant GAPDH mRNA level in the GBM cells transfected with ATN-RNA. It is absolutely evident that dsRNA specifically down regulates the tenascin-C gene expression and tumor growth (FIG. 7A). To confirm that we used also two control scrambled siRNAs in ex vivo GBM cells transfection experiments. The high selectivity of TN-C inhibition with ATN-RNA in contrast to siRNA of unrelated sequence (scrambled siRNAs) is seen (FIG. 7B, lanes 3 and 4). Above 80% degradation of TN-C mRNA was observed in GBM cells transfected with ATN-RNA (FIGS. 7A and B, lanes 4). As a positive control of that effect we analysed of GAPDH mRNA expression level in all cases (FIGS. 7A and C). All these data clearly demonstrate that ATN-RNA specifically knockdown TN-C mRNA synthesis in GBM tissue with a very high efficiency and extent significantly the survival time of patient. The tumor suppression observed mainly around the sites of ATN-RNA injection but not in remote area can suggest either a short distance migration of ATN-RNA or short lifetime of dsRNA.

Time dependent stability of ATN-RNA in GBM tissue extract is shown on the FIG. 8 and analysis of $^{32}$P-labeled ATN-RNA (163 bp) hydrolyzed products with human DICER on 10% polyacrylamide gel electophoresis with 7 M urea is presented on the FIG. 9.

The differences in the observed effects of ATN-RNA in the six subjects studied in this paper, can be due to the size of a non-removable tumor tissue. A neoplasm in case No. 1, Tab. 1, was bigger compared to that of case No. 3, tab. 1 and its substantial part was not removed. Therefore, the amount of dsRNA could be reconsidered in the future. One can also think about other methods for dsRNA delivery, e.g., craniotomy and intracerebral injections [[9, 10, 12, 13]. Those approaches have however some limitations due to diffusion and difficulty to deliver RNA directly to cancer cells within the brain. We think that the application of therapeutic dsRNA to brain cancer cells through transvascular system20 is a very perspective approach. Therefore, we applied a combination of neurosurgery to remove the majority of the tumor and then the direct injection of RNA into remaining cancer cells. This approach we named interference RNA intervention (iRNAi).

TABLE 5

Distribution of patient with brain tumor and ATN-RNA application based on age and sex. The table was completed for 46 patients.

| Patients age (yrs) | Female | | Male | | All patients (46) | |
|---|---|---|---|---|---|---|
| | No. of patients | Patients (%) | No. of patients | Patients (%) | No. of patients | Patients (%) |
| ≤20 | — | — | 1 | 3.8 | 1 | 2.2 |
| 21-30 | 1 | 5 | — | — | 1 | 2.2 |
| 31-40 | 2 | 10 | 3 | 11.5 | 5 | 10.8 |
| 41-50 | 8 | 40 | 8 | 30.8 | 16 | 34.8 |
| 51-60 | 5 | 25 | 9 | 34.6 | 14 | 30.4 |
| ≥60 | 4 | 20 | 5 | 19.3 | 9 | 19.6 |

TABLE 6

Number of patients treated with ATN RNA for which the TNM classification of tumors was determined.

| TNM grade | No. of patients | Patients (%) |
|---|---|---|
| T1 M0 | 12 | 26.1 |
| T2 M0 | 19 | 41.3 |
| T3 M0 | 9 | 19.6 |
| T4 M0 | 6 | 13.0 |

Differences in survival times according to histopathology diagnosis are presented on FIG. 10 as a graph.

Patients suffering from brain tumor qualified for surgery and molecular intervention were managed at the Department of Neurosurgery and Neurotraumatology, University of Medical Sciences in Poznan. Precise tumor localization was determined with computerized tomography (CT) or magnetic resonance imaging (MRI), before every surgical procedure. We analyzed 48 patiens with brain tumor and diagnosed according to WHO criteria. They showed 25 primary WHO IV, 7 WHO III and 14 WHO II. After surgical resection RNAi was injected into postoperative area.

Efficacy of ATN-RNA treatment was estimated on the basis of follow-up studies including general and neurological condition as well as neuroimaging studies with the CT and MRI measured for each two month periods after the treatment. The consent for the treatment was obtained from patients—these data are presented in FIG. 11-FIG. 15.

REFERENCES

1. Van den Bent M J, Stupp R, Brandes A A, Lacombe D. Current and future trials of the EORTC brain tumor group. Onkologie 2004; 27:246-50.
2. Chiquet-Ehrismann R, Chiquet M. Tenascins; regulation and putative functions during pathological stress. Journal of Pathology 2003; 200:488-99,
3. Ilicke B J, Marion C, Chang Y F, Gould T, Lytton C K, Parma D, et al. Tenascin-C aptamers are generated using tumor cells and purified protein. Journal of Biological Chemistry 2001; 276:4844-54.
4. Pas J, Wyszko E, Rolle K, Rychlewski L, Nowak S, Zukiel R, Barciszewski J. Analysis 4 of structure and function of tenascin-C. Int J Biochem Cell Biol. 2006, 38(9):1594-602.
5. Behrem S, Zarkovie K, Eskinja N, Jonjic N. Distribution pattern of tenascin-C in glioblastoma: correlation with angiogenesis and tumor cell proliferation. Pathology Oncology Research 2005; 11:229-35.
6, Prawitt D. RNAi knock-down mice; an emerging technology for post-gnomic functional genetics. Cytogenetic Genome Research 2004; 105; 412-21.
7. Caplen N J. Gene Therapy Progress And Prospects. Down-regulation gene expression; the impact of RNA interference. Gene Therapy 2004; 11:1241-8.
8. Hall J. Unravelling the general properties of siRNAs: strength in numbers and lessons from the past. Nature Reviews Genetics 2004; 5:552-7.
9. Soutschek J, Akinc A, Bramlage B, Charisse K, Constien R, Donoghue M, et al. Therapeutic silencing of an endogenous gene by systemic: administration of modified siR-NAs. Nature 2004; 432:173-8.
10. Zimmermann T S, Lee A C, Akinc A, Bramlage B, Bumcrot D, Fedoruk M N, et al. RNAi-mediated gene silencing in non-human primates. Nature, published online., Mar. 26, 2006.
11. Pardridge W M. Intravenous, non-viral RNAi gene therapy of brain cancer, Expert Opinion on Biological Therapy 2004; 4; 1103-13.
12. Howard K. First Parkinson gene therapy trial launches. Nature Biotechnology 2003; 21:1117-8.
13. Caplen N J. RNAi quashes polyQ. Nature Medicine 2004; 10:775-6.
14. Fish R J, Kruithof E K O. Short-term cytotoxic effects and long-term instability of RNAi delivered using lentiviral vectors. BMC Molecular Biology 2004; 5:9.
15. Julio G I, Tenascin-C expression in the Cyst wall and fluid of human brain tumors correlates with angiogenesis. Neurosurgery 1997; 41; 1052-9.
16. Leung R K, Whittaker P A, RNA interference; from gene silencing to gene-specific therapeutics. Pharmacology & Therapeutics 2005; 107; 222-39.
17. Zhang H, Kolb P A, Jaskiewiez L, Westhof E, Filipowiez W. Single processing center models for human Dicer and bacterial RNase III. Cell 2004; 118:57-68.
18. Parrish S, Fleenur J, Xu S, Mello C, Fire A. Functional anatomy of a dsRNA trigger: differential requirement for the two trigger strands in RNA interference. Molecular Cell 2000; 6:1077-87.
19. Bhargava A, Dallman M F, Pearce D, Choi S. Long double-stranded RNA-mediated RNA interference as a 20. Lage H. Potential applications of RNA interference technology in the treatment of cancer. Future Oncology 2005; 3:103-113.
21. Zimmermann T S, Lee A C H, Akinc A, Bramlage B, Bumcrot D, Fedoruk M N, et al. RNAi-mediated gene silencing in non-human primates. Nature 2006; March 26; [Epub ahead of print].
22. Kang C S, Zhang Z Y, Jia Z F, Wang G X, Qiu M Z, Zhou H X, et al. Suppression of EGFR expression by antisense or small interference RNA inhibits U251 glioma cell growth in vitro and in vivo. Cancer Gene Therapy 2006; 13:530-538.
23. Dev K K. Using RNAi in the clinic. IDrugs 2006; 9:279-282.
24. Kumar P, Wu H, McBride J L, Jung K E, Kim M H, Davidson B L, Lee S K, Shankar P, Manjunath N. Transvascular delivery of small interfering RNA to the central nervous system. Nature. 2007, 448, 39-43.
25. Cantin E M, Rossi J J. Molecular medicine: entry granted. Nature. 2007, 448, 33-34.
26. Daniels D A, Chen H, Hicke B J, Swiderek K M, Gold L. A tenascin-C aptamer identified by tumor cell SELEX: systematic evolution of ligands by exponential enrichment. Proc. Natl. Acad. Sci. USA 2003, 100, 15416-15421.
27. Sarkar S, Nuttall R K, Liu S, Edwards D R, Yong V W. Tenascin-C stimulates glioma cell invasion through matrix metalloproteinase-12. Cancer Res 2006, 66, 11771-11780.
28. Leins A, Riva P, Lindstedt R, Davidoff M S, Mehraein P, Weis S. Expression of tenascin-C in various human brain tumors and its relevance for survival in patients with astrocytoma. Cancer 2003; 98:2430-9.
29. Pas J, Wyszko E, Rolle K, Rychlewski L, Nowak S, Zukiel R, Barciszewski J. Analysis of structure and function of tenascin-C. Int J Biochem Cell Biol. 2006, 38(9):1594-602.
30. Behrem S, Zarkovic K, Eskinja N, Jonjic N. Distribution pattern of tenascin-C in glioblastoma: Correlation with angiogenesis and tumor cell proliferation. Pathol Oncol Res 2005; 11:229-35.
31. Zukiel R., Nowak S., Wyszko E., Rolle K., Gawrońska I., Barciszewska M., Barciszewski J., Cancer Biology & Therapy 5:8, 1002-1007, August 2006]; ©2006 Landes Bioscience; Research Paper, Suppression of Human Brain Tumor with Interference RNA Specific for Tenascin-C.
32. Cantin E M, Rossi J J. Molecular medicine: entry granted. Nature. 2007, 448, 33-34.
33. Fire A, Xu S, Montgomery M K, Kostas S A, Driver S E, Mello C C. Potent and specific genetic interference by double-stranded RNA in *Caenorhabditis elegans*. Nature 1998, 391, 806-811.

The invention claimed is:

1. A sequence of double-stranded ATN-RNA (dsRNA) consisting of: a first strand and a complementary second strand, wherein the first strand is between 100 and 200 nt, wherein the first strand includes between 100 to 200 nt of a fragment of a tenascin-C mRNA sequence at nucleotides 406 to 569, wherein the second strand includes a complementary RNA sequence, wherein when the dsRNA sequence is applied to a human tumor smaller fragments of 20-25 nt form therefrom, which smaller fragments are operative to cause a decrease in the expression of the gene encoding tenascin-C, retarding tumor growth.

2. A sequence according to claim 1, wherein the first and second complementary strands of the dsRNA sequence comprise SEQ ID NO 1.

3. A sequence of double-stranded ATN-RNA (dsRNA), consisting of: a fragment with a complimentary RNA strand, wherein the fragment of 100 to 200 nt includes 163 nt of a tenascin-C mRNA sequence, at nucleotide positions 406-569, where the dsRNA sequence is usable in the treatment of human brain tumors, wherein the dsRNA sequence causes a decrease in the expression of the tenascin-C gene, retarding tumor growth.

4. A sequence according to claim 3, wherein the the fragment with the complimentary RNA strand comprises SEQ ID NO 1.

5. A kit for use in inhibiting cancer cell which expresses tenascin-C, comprising reagents and components for use in treating a brain tumor, wherein the kit comprises at least one two-stranded RNA (dsRNA) sequence that is less than or equal to 200 base pairs and which comprises a fragment of the tenascin-C mRNA sequence at nucleotides 406 to 569 with a complimentary RNA sequence, wherein the fragment with the complementary RNA sequence binds to tenascin-C in a therapeutically effective amount, wherein the at least one dsRNA sequence in the kit causes a decrease in the expression of the tenascin-C gene, and inhibition of tumor growth.

6. A kit according to claim 5, wherein the fragment with the complimentary RNA sequence comprises SEQ ID NO 1, and wherein the kit is used for a human brain tumor, including at least one of astrocytic brain tumors, Glioblastoma multiforme, Astrocytoma, Anaplastic astrocytoma, Anaplastic oligoastrocytoma, and Oligodendroglioma.

* * * * *